United States Patent [19]

Segelman

[11] Patent Number: 6,017,893
[45] Date of Patent: Jan. 25, 2000

[54] USE OF ISOFLAVONES TO PREVENT HAIR LOSS AND PRESERVE THE INTEGRITY OF EXISTING HAIR

[75] Inventor: Alvin B Segelman, Orem, Utah

[73] Assignee: Natures Sunshine Products, Inc.

[21] Appl. No.: 08/920,955

[22] Filed: Aug. 29, 1997

[51] Int. Cl.[7] ........................................... A61K 31/70
[52] U.S. Cl. .................... 514/27; 514/456; 514/880
[58] Field of Search ........................... 514/27, 456

[56] References Cited

U.S. PATENT DOCUMENTS

| | | | |
|---|---|---|---|
| 5,554,519 | 9/1996 | Weber et al. | 435/125 |
| 5,639,715 | 6/1997 | Kung | 514/456 |

FOREIGN PATENT DOCUMENTS

| | | |
|---|---|---|
| 5-78347 | 3/1993 | Japan . |
| 96/10387 | 4/1996 | WIPO . |

OTHER PUBLICATIONS

CA 126:282781, Matsura et al, Mar. 4, 1997.
CA 119:146570, Hakamata et al, Mar. 30, 1993.
CA 125:131320, Delgado, 1996.

*Primary Examiner*—Rebecca Cook
*Attorney, Agent, or Firm*—Parsons Behle & Latimer

[57] ABSTRACT

The present invention is an orally- or topically-administrable composition for preventing and treating hair loss. The invention is a plant or plant extract containing isoflavones having a weak estrogen activity. The invention further includes methods for using the invented composition to prevent and treat hair loss.

10 Claims, No Drawings

USE OF ISOFLAVONES TO PREVENT HAIR LOSS AND PRESERVE THE INTEGRITY OF EXISTING HAIR

This application is a continuation-in-part of U.S. provisional patent application Ser. No. 60/025,810, filed Aug. 30, 1996.

I. BACKGROUND OF THE INVENTION

A. Field of the Invention

This invention relates to the field of compositions and methods for treating and preventing hair loss. More specifically, this invention relates to compositions of isoflavone-containing plants and plant extracts which can be used to treat or prevent hair loss, and methods for making and using such compositions.

B. Description of Related Art

Hair loss is a common problem in both men and women. It has been shown that hair loss in humans can be associated with high circulating levels of the androgen testosterone. In these cases, hair loss occurs because the testosterone binding sites (receptors) in the scalp-hair regions are constantly occupied by testosterone.

One proposed method of treating hair loss is to administer an estrogen, like progesterone, to humans with "falling hair." Estrogen can also bind to the testosterone receptors in the scalp-hair regions. Because estrogen would compete with testosterone for binding to the testosterone receptors, the number of testosterone receptors occupied by testosterone would decrease. In this manner, the "hair loss" effect of testosterone is blocked and scalp hair is not lost. However, because of the undesirable feminizing effects of progesterone, especially in men, strong estrogens like progesterone are not used.

II. SUMMARY OF THE INVENTION

The present invention is based on the principle that plants and plant extracts containing isoflavones can inhibit hair loss. Plants or plant extracts containing isoflavones can be administered either orally or topically to prevent hair loss. When administered topically, the composition may also be combined with estrogens such as progesterone; the isoflavones mitigate the effects of strong estrogens.

The present invention provides the additional benefit that the administration of isoflavone-containing plants or plant extracts can provide other health benefits in addition to preventing hair loss. Another advantage of the invention is that the isoflavone-containing plants and plant extracts can be combined with other pharmaceutical treatments for preventing hair loss without adversely affecting the beneficial and positive effects of such treatments.

It is an object of the present invention to provide a method for preventing hair loss by using an isoflavone-containing composition.

It is another object of the invention to provide a method of improve and maintain the integrity of existing hair.

It is a further object of the invention to provide a method for preventing hair loss which avoids artificially coloring the hair.

It is still another object of the invention to provide a method of preventing hair loss which may be used topically.

It is a further object of the invention to provide a method of preventing hair loss which may be used orally.

These and other objects, features and advantages of the invention will be clear to a person of ordinary skill in the art upon reading this specification.

III. DETAILED DESCRIPTION OF A PREFERRED EMBODIMENT

Isoflavonoids are one of the sub-groups of a large class of naturally occurring substances known as flavonoids. The isoflavonoids all possess the basic structure of isoflavone (I), and the individual isoflavonoids mainly correspond to substituents made usually at the positions 5, 6, 7, 2', 3', 4' and 5' on the isoflavone nucleus.

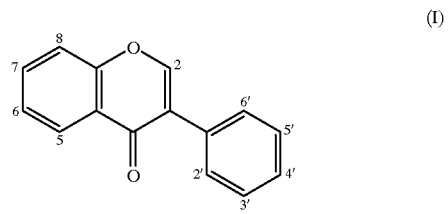

(I)

The functional groups include —OH, —OCH$_3$, and methylenedioxy. Frequently one or more sugars is attached by means of glycosidic bonds (an isoflavonoid glycoside). Most isoflavonoid glycosides are quite soluble in water and much less soluble in organic solvents, while the isoflavonoid aglycones (i.e., the glycoside minus the sugars) differ widely in aqueous solubility depending on the nature of the substituents (i.e., less water solubility with increasing numbers of —OCH$_3$ and methylenedioxy functionalities). Most isoflavonoids can be extracted from plant material using water, water-alcohol mixtures and alcohol solvents, as will be appreciated by those of skill in the art.

Isoflavonoids occur in various concentrations in all plant parts (roots, stems, bark, seeds, leaves, sap (juice), flowers and fruits). The isoflavonoids are distributed in many plant families (Leguminosae, Rosaceae, Podocarpaceae, Iridaceae, Moraceae, Amarantaceae and Compositae) and are found with great frequency in the Leguminosae.

A. COMPOSITION OF THE INVENTION

The present invention is based on the principle that plants or plant extracts containing isoflavones may be administered orally or topically to prevent hair loss. Isoflavones exhibit many biological activities, including insecticidal, pesticidal, antifungal and estrogenic activities. It is this last property, estrogenic (female hormone) activity, to which this invention pertains.

The isoflavones of the present invention include those which exhibit estrogenic activity and which bind to testosterone receptors. Such isoflavones prevent the "hair loss" effect of testosterone by inhibiting the binding of testosterone to the hair and scalp receptor, thereby resulting in maintenance of scalp hair integrity. Additionally, the unwanted side effects, such as feminization, observed for "strong" estrogens would be eliminated because isoflavones within the scope of the present invention exhibit only a weak estrogenic activity.

The present invention includes compositions containing isoflavones in general, and particularly soybean isoflavonoids, may be used to prevent hair loss in mammals, including both in men and women, by the aforementioned mechanism of action. Such isoflavones may include, but are not limited to, genistein (II) and variants thereof. Genistein is also termed 5,7-dihydroxy-3-(4-hydroxyphenyl)-4H-1-benzopyran-4-one or 4',5,7-trihydroxy-isoflavone.

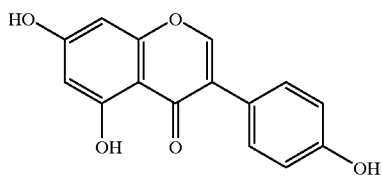

(II)

In the most preferred embodiment of the invention, the isoflavones are of the following formula:

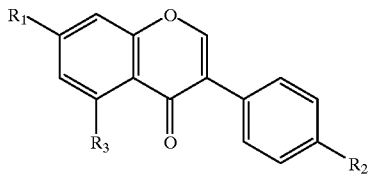

(III)

Wherein $R_1$, $R_2$ and $R_3$ are independently selected from hydroxyl, hydroxymethyl and sugars such as glucose.

In another preferred embodiment of the invention, the preferred isoflavones are of the following formula:

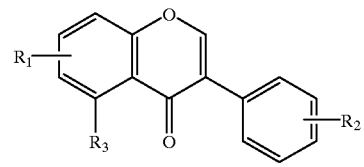

(IV)

Wherein $R_1$, $R_2$ and $R_3$ are independently selected from hydroxyl, hydroxymethyl and sugars such as glucose. $R_1$ may be located at the 6, 7 or 8 positions. $R_2$ may be located at the 3', 4' 5' or 6' positions.

It is contemplated that the isoflavones of the present invention, either in highly purified form or in a mixture with other phytoconstituents (extracts) could be used in various forms including, but not limited to, capsules, tablets, liquids and powders intended for internal use, and lotions, creams, ointments and solutions for topical use to be applied to the scalp regions in need of treatment.

In a more preferred embodiment of the invention, a topical formulation of the preferred isoflavones is free of phytoconstituents which artificially color hair. Such phytoconstituents can be removed by separation of the preferred isoflavones from the contaminating colorants.

Sources of the preferred isoflavones include soy and other members of the Leguminosae family and the Rosaceae, Podocarpaceae, Iridaceae, Moraceae, Amarantaceae and Compositae families, as will be appreciated by those in the art.

B. EXTRACTION AND PURIFICATION

Generally, isoflavonoids can be extracted from plant material using various hydroalcoholic solvents, after which the solvent can be removed to leave a plant extract rich in isoflavonoids. This procedure is the simplest method but the isoflavonoids are highly contaminated by various phytoconstituents in the extract. When purification is desired, the above prepared extract can be subjected to various types of column chromatography using, but not limited to, silicic acid, silica gel, cellulose powder, Magnesol and polyamide, and by eluting the desired isoflavonoids with various solvents and solvent mixtures. The following examples using soybeans (but applicable to all plant materials) demonstrate the procedures used to extract and prepare semi-purified extracts rich in isoflavones, including genistein (II).

i. Extraction:

Coarsely ground soybeans (dried or fresh) are first defatted by extraction with petroleum ether. The defatted beans are exhaustively extracted with 50–80 percent ethanol and the extracts concentrated to a sirup in vacuo.

ii. Purification:

The concentrated extract is subjected to column chromatography using one or more of the following methods:

a. Silica gel—The concentrated extract is applied to the top of a column packed with water-wet silica gel. Elution is carried out with the organic phase from an ethyl acetateformic acid-water mixture (8:2:3). Collected fractions containing isoflavones (detected by thin layer chromatography (TLC)) are combined and evaporated to dryness to afford an isoflavone-rich soybean extract enriched in genistein (II) and other isoflavones.

b. Cellulose Powder—The concentrated extract is applied to the top of a column packed as a cellulose-water slurry. Elution is carried out using the organic phase from a butanolacetic acid-water mixture (4:1:1). The collected fractions containing isoflavones (detected by TLC) are combined and evaporated to dryness to afford an isoflavone-rich soybean extract enriched in genistein (II) and other isoflavones.

c. Cation-exchange Resins—The concentrated extract is applied to the top of a column packed as an aqueous slurry of the resin in the H-form. Useful resins include, but are not limited to, Amberlite IRC-50, Duolite Cation Selector CS-100, Duolite I-XT, Amberlite 4.5 and Amberlite IR-4B. Water-soluble salts, sugars and acids can be removed by repeated water washing of the column. Elution of the column using 20 percent aqueous ethanol removes first the isoflavone glycosides, such as genistin. Next, elution with 95 percent ethanol removes aglycones, such as genistein (II). Isoflavone-rich eluates (TLC) are combined and evaporated to give extracts rich in genistin or genistein, respectively.

d. Polyamide (Powdered Nylon)—The concentrated extract is adsorbed to the top of a column packed as an aqueous slurry of polyamide. Elution is carried out using water containing increasing amounts of ethanol or acetone. Isoflavone-rich elevates (TLC) are combined and evaporated to give a genistein enriched soybean extract.

iii. Synthesis:

Genistein may be synthesized by fermentation a soy-based extract using *Saccharopolyspora erythracea*, as disclosed in U.S. Pa. No. 5,554,519. This patent is incorporated by reference herein. Briefly, a soy-based extract, from soybean meal, flour, oil or grits, is supplement with a culture or fermentation medium and then inoculated with *Saccharopolyspora erythracea*. Fermentation occurs from between about 10° C. to about 40° C., as disclosed in the cited reference. Fermentation occurs from about 20 to about 250 hours, as will be appreciated by those of skill in the art.

After fermentation, genistein is extracted by first adjusting the pH of the fermentation medium to between about 8 and 11. The medium is then extracted with an organic solvent, such as alcohols, ethers, ketones, alkyl esters of fatty acids and chlorinated hydrocarbons, as disclosed in the cited reference. Such extraction procedures are also well known in the art.

After extraction, genistein is separated from other compounds in the organic extract by procedures which are well-known in the art. Such separation procedures may include reextraction with acidified organic solvent, solvent evaporation, high pressure liquid chromatography (HPLC) and FPLC.

C. METHOD OF MAKING ORAL DOSAGE FORMS

Orally-administrable dosage forms of the invention may include, but are not limited to, capsules, tablets, powders and liquids (hereinafter referred to as "oral dosage forms"). Other equivalent oral dosage forms are within the scope of the invention, as will be readily appreciated by those of skill in the art. As an oral dosage form, the composition may be administered alone or in combination with food. Oral dosage forms may contain the preferred isoflavones alone or in combination with one or more herbs or herb extracts. In a preferred embodiment of the invention, an oral dosage form contains from about 10 to about 900 mg total weight of plant or plant extract. In a more preferred embodiment of the invention, an oral dosage form contains from about 250 to about 750 mg total weight of plant or plant extract. In a still more preferred embodiment of the invention, an oral dosage form contains from about 400 to about 500 mg total weight plant or plant extract. In the most preferred embodiment, the oral dosage will contain about 450 mg of isoflavone-containing plant or plant extract. If a liquid extract is used, the liquid extract can be calibrated by determining the dry mass of the plant or plant extract contained in a given volume of liquid extract.

The isoflavone-containing plant or plant extract may be beneficially mixed with inert carriers. Suitable inert carriers may include inter alia maltodextrin, beet root fiber and tomato fiber. The isoflavone-containing plant or plant extract may also beneficially be admixed with various inactive excipients, carriers, diluents, lubricants and other so-called "pharmaceutical aids" (adjuvants) and then formed into capsules and tablets. Examples of inactive excipients, carriers, diluents, lubricants, disintegrants, and so-called "pharmaceutical aids" include, but are not limited to, the following: silica, silica gel, cellulose and microcrystalline cellulose, cross-carmelose sodium, dicalcium phosphate, various gums (such as acacia, tragacanth, guar, and xanthan), alginic acid, sodium alginate, corn syrup solids, rice syrup solids, maltodextrin, hydroxypropylcellulose, hydroxypropylmethyl cellulose, corn and potato starches and other plant starches, modified potato starch, stearins, stearic acid, carboxymethyl cellulose, sodium carboxymethyl cellulose, dextrose, fructose, bone meal, oyster shell, isolated soy protein, potassium carbonate, sodium starch glycolate, sorbitol, talc, methylcellulose, polyethylene glycol 400 and other polyethylene glycols, sorbic acid and potassium sorbate, sodium lauryl sulfate, sodium phosphate monobasic, sodium sulfate, potassium bicarbonate, mannitol, lactose, corn flower, zinc gluconate, zinc oxide, xylitol, calcium silicate, sodium ascorbate, citric acid, calcium carbonate, carnauba wax, oils (natural, partial or fully hydrogenated, such as olive oil, peanut oil, cottonseed oil, rape-seed oil, corn oil), magnesium stearate and plant fibers including, but not limited to, beet root fiber and tomato fiber. Additional inactive excipients, carriers, diluents, lubricants and adjuvants which may be used with the enzyme composition are disclosed in Remington's Pharmaceutical Sciences, Ed. 18 (A.R. Gennaro, ed., Mack Publishing Co., Easton, Pa., 1990) and in the Handbook of Pharmaceutical Excipients, Ed. 2 (A. Wade and P. J. Weller, eds., American Pharmaceutical Association, Washington, D.C., and the Pharmaceutical Press, London Publishers, 1994), both of which are incorporated by reference herein in their entirety.

The total amount of plant, plant extract, carriers, excipients, diluents, lubricants and other so-called "pharmaceutical aids" included in an oral dosage form may be varied according to the preferred size of the oral dosage form. For capsules, the total weight may range from about 275 mg to about 500 mg, although greater or lesser capsule weights are within the scope of the invention. For tablets, the total weight may range from about 400 to about 450 mg, although greater or lesser weights are within the scope of the invention.

Topically-administrable forms of the invention may include ointments, creams, lotions or other solutions. The dosage ranges for topically administrable forms are equivalent to those for the oral forms. Methods of making such topically-administrable creams, lotions, ointments and solutions are known in the art. For topical administration, the composition may be used alone or in combination with estrogen hormones. When combined with an estrogen hormone, progesterone is the preferred hormone. Topical compositions may contain up to about 5 mg progesterone per 30 grams or 30 milliliters of topical lotion, cream, ointment or solution.

For the manufacture of capsules, tablets and powders, it is suitable to mix the appropriate amounts of the plant or plant extract alone or with required adjuvants, followed by mixing in a blender or other suitable mixing equipment to afford a homogeneous and powdered free flowing mixture which can then be encapsulated or tableted using suitable equipment. Encapsulation and tableting procedures are well-known to those of skill in the art. These procedures are also disclosed in Remington's Pharmaceutical Sciences, Ed. 18, op cit. (especially pages 1615–1675) and in the Handbook of Pharmaceutical Excipients, Ed. 2, op cit., both of which are incorporated by reference herein in their entirety.

For the manufacture of tablets using a wet granulation process, the mixture may be combined, wet-granulated, dried and suitably ground to the desired particle size. The resultant mixture may then be ground and/or mixed using suitable equipment to afford a homogeneous mixture which is then conveniently pressed into tablets of the desired weight and shape using suitable equipment.

Wet granulation processes for tableting are well-known to those of skill in the art. These procedures are also disclosed in Remington's Pharmaceutical Sciences, Ed. 18, op cit., and in the Handbook of Pharmaceutical Excipients, Ed. 2, op cit, which are incorporated by reference herein in their entirety.

Powdered forms of the composition will prepared according to the same procedures which are used for capsules, except that the powder will not be encapsulated. Powdered forms may also be prepared by grinding tablets.

D. METHOD OF USING THE COMPOSITION

In its oral form, the composition may be taken alone or in combination with food or liquids. In the preferred embodiment of the invention, the composition is preferably taken with a meal or with liquid. Generally from 1 to 2 oral doses may be taken in from 1 to 4 or more times a day. Powdered forms of the invention may be consumed by dissolving or suspending the powder in water or other suitable beverage. Topically administrable forms are applied in similar amounts.

E. EXAMPLES OF COMPOSITIONS

The following examples are contemplated to be the best mode of making the invention, although the invention is not intended to be limited by or to these embodiments.

EXAMPLES

Internal Use:
  i. Capsules: Each capsule to contain:
     1. Powdered, defatted soybeans—450 mg.
     2. Concentrated, semi-purified soybean extract containing 20–50% or more total isoflavones—450 mg.

The required amount (scale-up) of the prepared and mixed formulation is used to fill gelatin capsules using suitable equipment, as is readily known to those of skill in the art.

ii. Tablets: Each tablet to contain:
     1. Powdered, defatted soybeans—450 mg with tablet excipient sufficient to make one standard tablet
     2. Concentrated, semi-purified soybean extract containing 20–50% or more total isoflavones—450 mg with tablet excipient base, sufficient to make one standard tablet.

The required amount (scale-up) of the prepared and mixed above formulation is pressed directly into tablets (for example, 7/16" standard round) using suitable equipment, which is known to those of skill in the art.

iii. Liquids:
     1. Concentrated, semi purified soybean extract containing 20–50% or more total isoflavones—13.5 grams—and Aromatic Elixir, NF in a sufficient quantity to make 450 ml.
        Dose: one tablespoonful (about 15 ml) as needed.

iv. Bulk powdered formula:
  per teaspoon:
     1. Powdered, defatted soybeans—450 mg—with bulk powder excipient in a sufficient quantity such that each teaspoonful of final product contains about 450 mg of soybean.
     2. Concentrated, semi-purified soybean extract containing 20–50% or more total isoflavones—450 mg—with bulk powder excipient in a sufficient quantity such that each teaspoonful of final product contains about 450 mg of extract.
        Directions: mix 1–2 teaspoonsful in 6–8 ounces of liquid (milk, juice, water)

External Use:
  v. Ointments and Creams:
     1. Concentrated semi-purified soybean extract containing 20–50% or more total isoflavones—3–6 g—with an ointment or cream base vehicle in sufficient quantity to make 60 g.
     2. Concentrated, semi-purified soybean extract containing 20–50% or more total isoflavones—3–6 g—with up to about 5 mg per ounce progesterone and an ointment or cream base vehicle to make 60 g.
  6. Lotions:
     1. Concentrated, semi-purified soybean extract containing 20–50% or more total isoflavones—6–12 g—with a lotion base in a sufficient quantity to make 120 ml.
     2. Concentrated, semi-purified soybean extract containing 20–50% or more total isoflavones—6–12 g—with up to about 5 mg/30 ml progesterone and a lotion base in a sufficient quantity to make 120 ml.
  vii. Solutions:
     1. Concentrated semi-purified soybean extract containing from 20–50% or more total isoflavones, 12–24 grams, and a solution base in a sufficient quantity to dissolve and make 240 ml.
     2. Concentrated semi-purified soybean extract containing from 20–50% or more total isoflavones, 12–24 grams, up to about 5 mg progesterone per 30 ml, and a solution base in a sufficient quantity to dissolve and make 240 ml.

While the present invention has been described and illustrated in conjunction with a number of specific embodiments, those skilled in the art will appreciate that variations and modifications may be made without departing from the principles of the invention as herein illustrated and described.

The invention may be embodied in other specific forms without departing from the spirit or essential characteristics thereof. The present embodiments are to be considered in all respects as illustrative, and not restrictive.

I claim:

1. A method of treating hair loss, comprising:
   administering to a mammal in need thereof an effective amount of an isoflavone of the following formula:

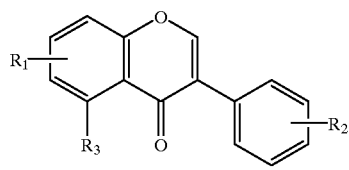

wherein $R_1$, $R_2$ and $R_3$ are independently selected from hydroxyl, hydroxymethyl and a sugar; and
   whereby said administration prevents hair loss.

2. The method of claim 1, wherein said isoflavone is of the formula:

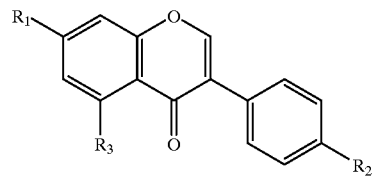

wherein $R_1$, $R_2$ and $R_3$ are independently selected from hydroxyl, hydroxymethyl and a sugar.

3. The method of claim 2, wherein said isoflavone is genistein.

4. The method of claim 1, wherein said isoflavone is a glycoside.

5. The method of claim 4, wherein said isoflavone is genistin.

6. The method of claim 1, wherein said isoflavone is an aglycone.

7. The method of claim 1, wherein said administration is topical.

8. The method of claim 7, further comprising administering an estrogen.

9. The method of claim 1, wherein said administration uses an oral dosage form.

10. The method of claim 1, wherein said isoflavone is isolated from a plant of the family consisting of Leguminosae, Rosaceae, Podocarpaceae, Iridaceae, Moraceae, Amarantaceae and Compositae.

* * * * *